(12) United States Patent
Giszter

(10) Patent No.: US 11,504,524 B2
(45) Date of Patent: Nov. 22, 2022

(54) MULTI-SITE PROBE AND COMBINATORIC METHOD

(71) Applicant: Drexel University, Philadelphia, PA (US)

(72) Inventor: Simon Francis Giszter, Havertown, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/759,441

(22) PCT Filed: Sep. 14, 2016

(86) PCT No.: PCT/US2016/051709
§ 371 (c)(1),
(2) Date: Mar. 12, 2018

(87) PCT Pub. No.: WO2017/048828
PCT Pub. Date: Mar. 23, 2017

(65) Prior Publication Data
US 2018/0178000 A1    Jun. 28, 2018

Related U.S. Application Data

(60) Provisional application No. 62/218,423, filed on Sep. 14, 2015.

(51) Int. Cl.
*A61N 1/05*      (2006.01)
*A61B 5/00*      (2006.01)
(Continued)

(52) U.S. Cl.
CPC .......... *A61N 1/0529* (2013.01); *A61B 5/0084* (2013.01); *A61B 5/291* (2021.01); *A61B 5/4058* (2013.01); *A61B 5/4064* (2013.01); *A61B 5/6864* (2013.01); *A61B 5/6868* (2013.01); *A61N 1/0551* (2013.01); *A61N 5/0601* (2013.01); *A61N 5/0622* (2013.01);
(Continued)

(58) Field of Classification Search
CPC ...... A61N 1/05; A61N 1/0529; A61N 1/0551; A61B 5/042; Y10T 29/49194
USPC ................................ 607/3, 89, 116; 600/377
See application file for complete search history.

(56) References Cited

U.S. PATENT DOCUMENTS 7,883,535 B2    2/2011   Cantin et al.
8,475,506 B1    7/2013   Bendett et al.
(Continued)

OTHER PUBLICATIONS

Kim, T. G.. Braided multi-electrode probes (BMEPs) for neural interfaces (Order No. 3568650). 2013. Available from ProQuest Dissertations & Theses Global. (1418268452). Retrieved from https://search.proquest.com/docview/1418268452?accountid=14753 (Year: 2013).*

(Continued)

*Primary Examiner* — Jon Eric C Morales
(74) *Attorney, Agent, or Firm* — Schott, P.C.

(57) ABSTRACT

A multi-site probe for interfacing with the central nervous system includes one more structures disposed perpendicularly on a backing layer, where each structure includes a braided sleeve over a flexible or rigid core, and a delivery-vehicle. The structures may include optrodes and electrodes. The location of the probe may be determined through the application of combinatorics.

19 Claims, 6 Drawing Sheets

(51) Int. Cl.
A61N 5/06 (2006.01)
A61B 5/291 (2021.01)
A61B 5/24 (2021.01)
(52) U.S. Cl.
CPC . *A61B 5/24* (2021.01); *A61B 5/72* (2013.01); *A61N 2005/063* (2013.01)

(56) References Cited

U.S. PATENT DOCUMENTS

| | | | |
|---|---|---|---|
| 8,534,176 | B2 | 9/2013 | Giszter et al. |
| 8,639,311 | B2 | 1/2014 | Giszter |
| 8,936,630 | B2 | 1/2015 | Denison et al. |
| 2009/0099441 | A1 | 4/2009 | Giszter et al. |
| 2011/0295331 | A1 | 12/2011 | Wells et al. |
| 2012/0197374 | A1 | 8/2012 | Vogt et al. |
| 2012/0253261 | A1 | 10/2012 | Poletto et al. |
| 2014/0142664 | A1 | 5/2014 | Roukes et al. |

OTHER PUBLICATIONS

Kim, Tae Gyo, "Braided Multi-Electrode Probes (BMEPs) for Neural Interfaces," published in Dissertation Abstracts International, vol. 74-10 (E), Section: B.; p. 177; Publication No. AAT 3568650; ISBN: 9781303233005; ProQuest Dissertations And Theses; Thesis (Ph.D.)—Drexel University, 2013, pp. 1-159.
PCT, International Search Report for PCT/US16/51709, dated Dec. 6, 2016.
PCT, Written Opinion of the International Searching Authority for PCT/US16/51709, dated Dec. 6, 2016.
Anikeeva, P., et al., "Optetrode: a multichannel readout for optogenetic control in freely moving mice," Nat Neurosci., vol. 15, No. 1, pp. 163-170 (2011).
Bediz, B., et al., "Dissolvable microneedle arrays for intradermal delivery of biologies: fabrication and application," vol. 31, No. 1, pp. 117-135 (2014).
Bell, A.J., and Sejnowski, T.J., "An information-maximization approach to blind separation and blind deconvolution," Neural Computation, vol. 7, No. 6, pp. 1129-1159 (1995).
Blanche, T.J., et al., "Polytrodes: high-density silicon electrode arrays for large-scale multiunit recording," Journal of Neurophysiology, vol. 93, No. 5, pp. 2987-3000 (2005).
Branner, A., et al., "Long-term stimulation and recording with a penetrating microelectrode array in cat sciatic nerve," IEEE Transactions on Biomedical Engineering, vol. 51, No. 1, pp. 146-157 (2004).
Brian, R., et al., "The brain tissue response to implanted silicon microelectrode arrays is increased when the device is tethered to the skull," J Biomed Mater Res A, vol. 82, No. 1, pp. 169-178 (2007).
Brown, G.D., et al., "Independent components analysis (ICA) at the neural cocktail party," Trends Neuroscience, vol. 24, No. 1, pp. 54-63 (2001).
Canales, A., et al., "Multifunctional fibers for simultaneous optical, electrical and chemical interrogation of neural circuits in vivo," Nature Biotechnology, vol. 33, No. 3, p. 277-286 (Mar. 2015).
Coifman, R., and Wickerhauser, M.V., "Entropy-Based Algorithms for Best Basis Selection," IEEE Transactions on Information Theory, vol. 38, No. 2, pp. 713-718 (1992).
Desai, S.A., et al., "Improving impedance of implantable microwire multi-electrode arrays by ultrasonic electroplating of durable platinum black," Front Neuroeng, vol. 3, Article 5, pp. 11 (2010).
Ferguson, J.E., et al., "Creating low-impedance tetrodes by electroplating with additives," Sensors and Actuators A Physical, vol. 156, No. 2, pp. 388-393 (2009).
Gage, G.J., et al., "Surgical implantation of chronic neural electrodes for recording single unit activity and electrocorticographic signals," J Vis Exp, Issue 60, pp. 1-4 (2012).
Gerstein, G. L., and Clark, W.A., "Simultaneous Studies of Firing Patterns in Several Neurons," Science, vol. 143, No. 3612, pp. 1325-1327 (Mar. 1964).

Ghyomm, "An "electro-endoscope" for combined imaging, photocontrol and electrical recording," posted on Jul. 14, 2012, accessed at http://openoptogeneticsblog.org/?p=252, accessed on Jun. 18, 2015, pp. 1-5.
Gray, C.M., et al., "Tetrodes markedly improve the reliability and yield of multiple single-unit isolation from multi-unit recordings in cat striate cortex," J Neurosci Methods, vol. 63, pp. 43-54 (Dec. 1995).
Han, M., et al., "In vivo validation of custom-designed silicon-based microelectrode arrays for long-term neural recording and stimulation," IEEE Transactions on Biomedical Engineering, vol. 59, No. 2, pp. 346-354 (Feb. 2012).
Hart, C.B., and Giszter, S.F., "A neural basis for motor primitives in the spinal cord," J Neurosci, vol. 30, No. 4, pp. 1322-1336 (2010).
Hart, CB, and Giszter, S.F., "Modular premotor drives and unit bursts as primitives for frog motor behaviors," J Neurosci., vol. 24, No. 22, pp. 5269-5282 (2004).
Hochberg, L.R., et al., "Neuronal ensemble control of prosthetic devices by a human with tetraplegia," Nature, vol. 142, No. 7099, pp. 164-171 (2006).
Im, M., et al., "Neural Probes Integrated With Optical Mixer/Splitter Waveguides and Multiple Stimulation Sites," 2011 IEEE 24th International Conference on Micro Electro Mechanical Systems, pp. 1051-1054(2011).
Jäckel, D., et al., "Applicability of independent component analysis on high-density microelectrode array recordings," J Neurophysiol., vol. 108, No. 1, pp. 334-348 (2012).
Jaeger, D., et al., "A multiwire microelectrode for single unit recording in deep brain structures," J Neurosci Methods, vol. 32, pp. 143-148 (May 1990).
Kim, T., et al., "Braided multi-electrode probes: mechanical compliance characteristics and recordings from spinal cords," NIH Public Access, vol. 10, No. 4, 045001, pp. 22 (2013).
Kim, T., et al., "Braided multi-electrode probes: mechanical compliance characteristics and recordings from spinal cords," J Neural Eng. Author manuscript, vol. 10, No. 4, pp. 1-22 (2013).
Kipke, D.R., et al., "Advanced neurotechnologies for chronic neural interfaces: new horizons and clinical opportunities," J Neurosci, vol. 28, No. 46, pp. 11830-11838 (2008).
Kozai, T.D., et al., "Chronic tissue response to carboxymethyl cellulose based dissolvable insertion needle for ultra-small neural probes," Biomaterials, vol. 35, No. 34, pp. 9255-9268 (2014).
Kozai, T.D., et al., "Ultrasmall implantable composite microelectrodes with bioactive surfaces for chronic neural interfaces," Nature Materials, vol. 11, No. 12, pp. 1065-1073 (2012).
Kruger, J., et al., "Seven years of recording from monkey cortex with a chronically implanted multiple microelectrode," Front Neuroeng, vol. 3, Article 6, pp. 1-9 (2010).
Lansink, C.S., et al., "A split microdrive for simultaneous multi-electrode recordings from two brain areas in awake small animals," Journal of Neuroscience Methods, vol. 162, No. 1-2, pp. 129-138 (2007).
Lawrence, S. M., et al., "Acute peripheral nerve recording characteristics of polymer-based longitudinal intrafascicular electrodes,"IEEE Transactions on Neural Systems and Rehabilitation Engineering, vol. 12, No. 3, pp. 345-348 (2004).
Ludwig, K.A., et al., "Using a common average reference to improve cortical neuron recordings from microelectrode arrays," J Neurophysiol, vol. 101, No. 3, pp. 1679-1689 (2009).
Mallat, S., and Zhang, Z., "Matching pursuits with time-frequency dictionaries," IEEE Transactions on signal processing. Vol. 41, No. 12, pp. 3397-3415 (1993).
Misra, A., et al., "Preventing neuronal damage and inflammation in vivo during cortical microelectrode implantation through the use of Poloxamer P-188," J Neural Eng, vol. 10, No. 1, 016011, pp. 1-22 (2013).
Musallam, S., et al., "A floating metal microelectrode array for chronic implantation," J Neurosci Methods, vol. 160, No. 1, pp. 122-127 (2007).
Muthuswamy, J., et al., "Adaptive movable neural interfaces for monitoring single neurons in the brain," Frontiers in Neuroscience, vol. 5, Article 94, pp. 1-11 (2011).

(56) References Cited

OTHER PUBLICATIONS

Nagel, G., et al., "Channelrhodopsin-2, a directly light-gated cation-selective membrane channel," Proc Natl Acad Sci, vol. 100, No. 24, pp. 13940-13945 (2003).
Nicolelis, M.A., et al., "Chronic, multisite, multielectrode recordings in macaque monkeys," Proceedings of the National Academy of Sciences, vol. 100, No. 19, pp. 11041-11046 (2003).
Otchy, T.M., and Olveczky, B., "Design and assembly of an ultra-light motorized microdrive for chronic neural recordings in small animals," Journal of Visualized Experiments, Issue 69, e4314, p. 7 (2012).
Prasad, A., and Sanchez, J.C., "Quantifying long-term microelectrode array functionality using chronic in vivo impedance testing," J Neural Eng, vol. 9, No. 2, p. 026028 (2012).
Prasad, A., et al., "Comprehensive characterization and failure modes of tungsten microwire arrays in chronic neural implants," J Neural Eng, vol. 9, No. 5, 056015, pp. 1-21 (2012).
Qin, G., et al., "Fabrication of bio-microelectrodes for deep-brain stimulation using microfabrication and electroplating process," Microsystem Technologies, vol. 15, No. 6, pp. 933-939 (2009).
Rousche, P.J., and Normann, R.A., "A method for pneumatically inserting an array of penetrating electrodes into cortical tissue," Ann Biomed Eng, vol. 20, pp. 413-422 (1992).
Santors, L., et al., "A novel tetrode microdrive for simultaneous multi-neuron recording from different regions of primate brain," J Neurosci Methods., vol. 205, No. 2, pp. 368-374 (2012).
Sharma, A., et al., "Long term in-vitro functional stability and recording longevity of fully integrated wireless neural interfaces based on Utah Slant Electrode Array," J Neural Eng, vol. 8, No. 4, 045004, pp. 1-13 (Aug. 2011).
Skousen, J.L., et al., "Reducing surface area while maintaining implant penetrating profile lowers the brain foreign body response to chronically implanted planar silicon microelectrode arrays," Prog Brain Res, vol. 194, pp. 167-180 (2011).
Snellings, A., et al., "Improved signal and reduced noise in neural recordings from close-spaced electrode arrays using independent component analysis as a preprocessor," Journal of Neuroscience Methods, vol. 150, No. 2, pp. 254-264 (2006).
Song, W., and Giszter, S.F., "Adaptation to a cortex-controlled robot attached at the pelvis and engaged during locomotion in rats," J Neurosci., vol. 31, No. 8, pp. 3110-3128 (2011).
Song, W., et al., "Multiple types of movement-related information encoded in hindlimb/trunk cortex in rats and potentially available for brain-machine interface controls," IEEE transactions on biomedical engineering, vol. 56, No. 11 Pt 2, pp. 2712-2716 (2009).
Swindale, NV, and Spacek M.A., "Spike detection methods for polytrodes and high density microelectrode arrays," Journal of Computational Neuroscience, vol. 38, No. 2, pp. 249-261 (2014).
Szarowski, D.H., et al., "Brain responses to micro-machined silicon devices," Brain Res, vol. 983, pp. 23-35 (2003).
Takahashi, S., et al., "Automatic sorting for multi-neuronal activity recorded with tetrodes in the presence of overlapping spikes," J Neurophysiol., vol. 89, No. 4, pp. 2245-2258 (2002).
Tseng, W.T., et al., "A bundled microwire array for long-term chronic single-unit recording in deep brain regions of behaving rats," J Neurosci Methods, vol. 201, pp. 368-376 (2011).
Turner, J.N., et al., "Cerebral astrocyte response to micromachined silicon implants," Experimental Neurology, vol. 156, No. 1, pp. 33-49 (1999).
Vandecasteele, M., et al., "Large-scale recording of neurons by movable silicon probes in behaving rodents," Journal of Visualized Experiments, e3568, pp. 1-6 (2012).
Ward, M.P. et al., "Toward a comparison of microelectrodes for acute and chronic recordings," Brain Res, vol. 1282, pp. 183-200 (2009).
Winslow, B.D., and Tresco, P.A., "Quantitative analysis of the tissue response to chronically implanted microwire electrodes in rat cortex," Biomaterials, vol. 31, pp. 1558-1567 (Mar. 2010).
Yamamoto, J., and Wilson, M.A., "Large-scale chronically implantable precision motorized microdrive array for freely behaving animals," J Neurophysiol, vol. 100, No. 4, pp. 2430-2440 (2008).
Yizhar, O., et al., "Optogenetics in neural systems," Neuron, No. 71, No. 1, pp. 9-34 (2011).
Saleh, B., and Teich, M.C., "Fundamentals of Photonics," Wiley, NY., Part 1, pp. 1-14 (2007).
Saleh, B., and Teich, M.C., "Fundamentals of Photonics," Wiley, NY., Part 2, pp. 15-64 (2007).
Saleh, B., and Teich, M.C., "Fundamentals of Photonics," Wiley, NY., Part 3, pp. 65-114 (2007).
Saleh, B., and Teich, M.C., "Fundamentals of Photonics," Wiley, NY., Part 4, pp. 115-164 (2007).
Saleh, B., and Teich, M.C., "Fundamentals of Photonics," Wiley, NY., Part 5, pp. 165-214 (2007).
Saleh, B., and Teich, M.C., "Fundamentals of Photonics," Wiley, NY., Part 6, pp. 215-264 (2007).
Saleh, B., and Teich, M.C., "Fundamentals of Photonics," Wiley, NY., Part 7, pp. 265-307 (2007).

* cited by examiner

MULTI-SITE PROBE AND COMBINATORIC METHOD

STATEMENT REGARDING GOVERNMENT SUPPORT

This invention was made with government support under Contract No. NS072651 awarded by the National Institutes of Health. The government has certain rights in the invention.

BACKGROUND

The central nervous system (CNS) is one of the most important biological systems in any organism. The ability to accurately monitor the electrical activity of the central nervous system is important for diagnosing neurophysiological problems such as nerve diseases, sleep disorders, comas, encephalopathies, and brain death, and as such is a crucial element of modern medicine. A means of measuring electrical activity is the electrode, which pierces the neural tissue in order to interface directly with the nervous system. Another means of interfacing with the CNS originates from the field of optogenetics, which uses pulses of light to control and monitor the activities of individual neurons within living tissue. Optogenetic methods deliver light to such cells by means of an electrode analogue called an 'optrode.' However, a major constraint on current multielectrode and optrode designs is that interaction with the CNS is limited to one recording site per tether wire, or one release site per fiber optic light guide. The unique single site on the tether wire or 'optrode' places the recording or light delivery at a unique spatial location—chosen by the investigator or clinician. Each additional spatial site that is to be sampled requires another trace, tether wire or light-guide fiber as part of the implant.

Current conventional wisdom in extracellular recording is that ~1.3 neurons/units can be recorded per tether wire, in either single wire or tetrode arrangements. This limitation is more properly ~1.3 units at each recording wire site. In optogenetics, optic fibers acting as 'optrodes' are also usually limited to single release sites for the illuminating light at a location. In addition to this, current multielectrode and optrode designs suffer from relatively high long-term inflammatory responses, insufficient probe compliance and tolerance of micromotion, and inadequate means for precise deployment in deep brain, cortex, or spinal cord CNS targets. As such, there exists a distinct need for an electrode or optrode configuration that can address these deficiencies.

SUMMARY OF THE EMBODIMENTS

A multi-site probe for interfacing with the central nervous system includes one or more structures which may be disposed perpendicularly on a backing layer, where each structure comprises a braided sleeve over a flexible or rigid core, and a delivery-vehicle. The structures may include optrodes and electrodes. The location of the probe may be determined through the application of combinatorics.

DETAILED DESCRIPTION OF THE EMBODIMENTS

Multi-Site Probe

One constraint on probe design is that each wire or trace terminates in a single site, which gives high spatial specificity, but only ~1.3 neural units are on average recorded at each site. It is possible to overcome this limitation in carefully structured multielectrode or multioptrode probes. Combined with modern signal processing and electrode fabrication strategies, multi-site probes incorporating novel recording configurations may increase yield.

Stiff multi-site probes can be divided into four technologies: Silicon-based wafer or ceramic probes, 3D multi-tine geometries, and multiple tetrode assemblies in a microdrive, and microwire arrays. In addition, several other local and highly customized approaches are in use but are less widespread. Because of the size of these multi-site probes, pneumatics or other means may be used to place them into the brain or PNS. Flexible electrodes such as microwires, hatpin designs, tetrode wires, and conventional single electrodes are stiff enough to avoid buckling during implantation yet laterally flexible enough to comply somewhat with nervous tissue motion. While these probes can be chronically reliable, the exact spatial arrangement of many electrodes is difficult, increases infection risk, and implantation can take a long time.

The proposed multi-site probe stands to address these issues by reducing tissue inflammation, and facilitating controlled electrode/optrode site placements in combinations along the braid lengths. This apparatus is suitable for both wire and optic fiber recording and light deliver sites.

The braiding and sensing methods discussed herein may be further understood by reviewing U.S. Pat. Nos. 8,639,311 and 8,534,176, which share the same inventors as the current application and the contents of which are incorporated by references as if fully set forth herein.

A dissolvable polymer-based delivery-vehicle may be created by micro-fabrication and precision assembly techniques, and could also deliver drug or virus to targeted tissue during insertion.

Figure 1:
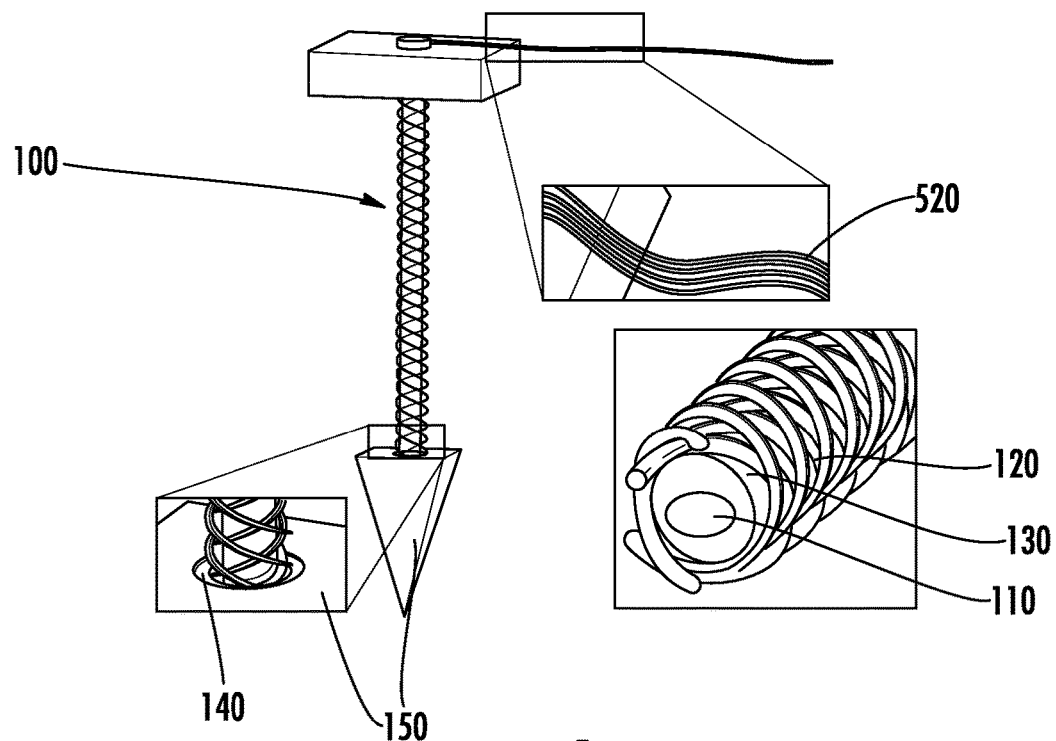
FIG. 1 shows the elements of an individual probe.
Figure 2:
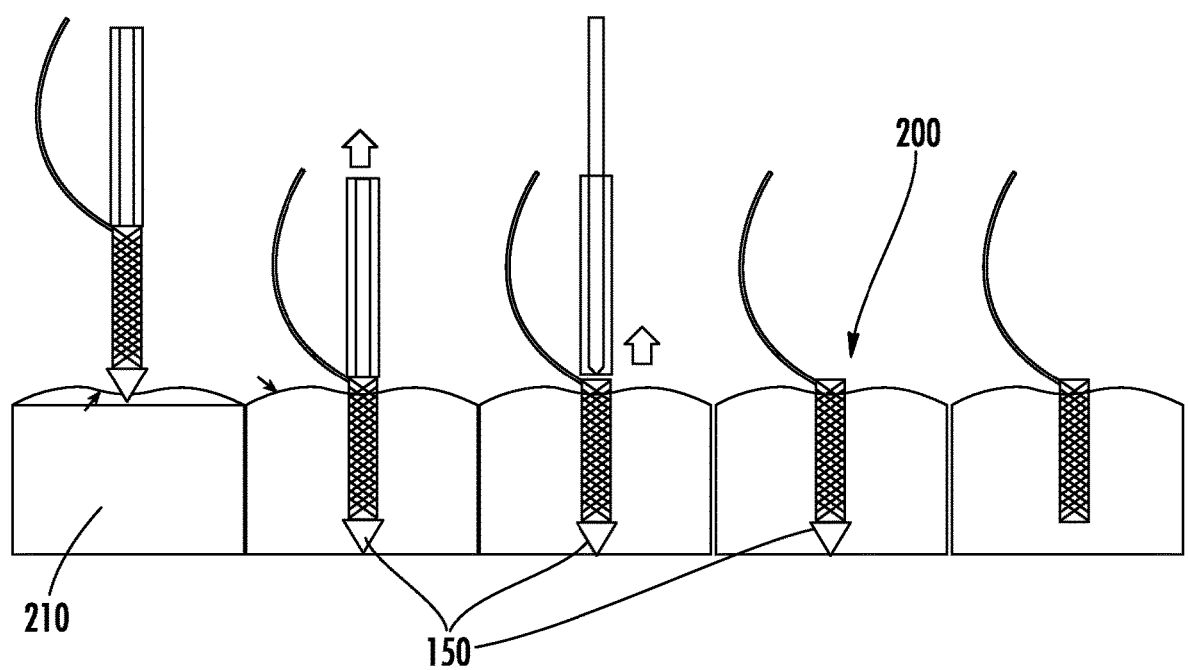
FIG. 2 shows the process by which the electrode is implanted in neural tissue.
Figure 3:
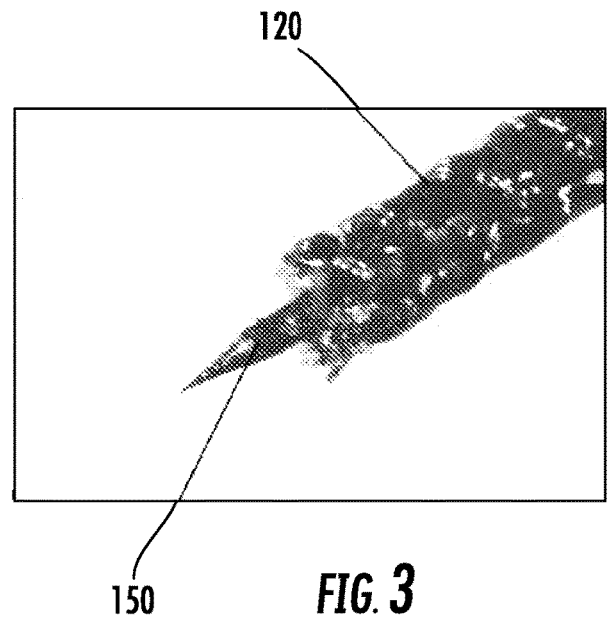
FIG. 3 shows the multi-site probe.

As shown in FIG. 1, each individual probe 100 may comprise a fine but stiff insertion wire 110, made of a material such as tungsten. Such a wire/probe can be made of any appropriate material and take other forms beyond those mentioned herein. Over the insertion wire 110, a braid 120 of ultra-fine electrically conducting wires or optic fibers in known geometries is disposed to form a thin compliant sleeve. As shown in FIG. 2 that shows insertion and removal of a wire/tip 110, this sleeve-like braided mesh 120 remains in the neural tissue 210 after the insertion wire is removed following insertion, as per step 200, allowing the electrodes/optrodes to be moved with the tissue 210 and, hence, reduce tissue reaction and increase stability. In FIG. 3, the braid 120 is on the left shown disposed around insertion wire 110, and on the right is shown after the insertion wire 110 withdraws from the braided sleeve 120. This braid 120 is comprised of ultrafine wires or optic fibers and such wires/fibers support geometries derived from the proposed combinatoric models, significantly reduce inflammation around the multi-site probe, and produce improvements in longevity of recording and operation, especially compared to larger (e.g. 50 micron) microwires.

Figure 4:
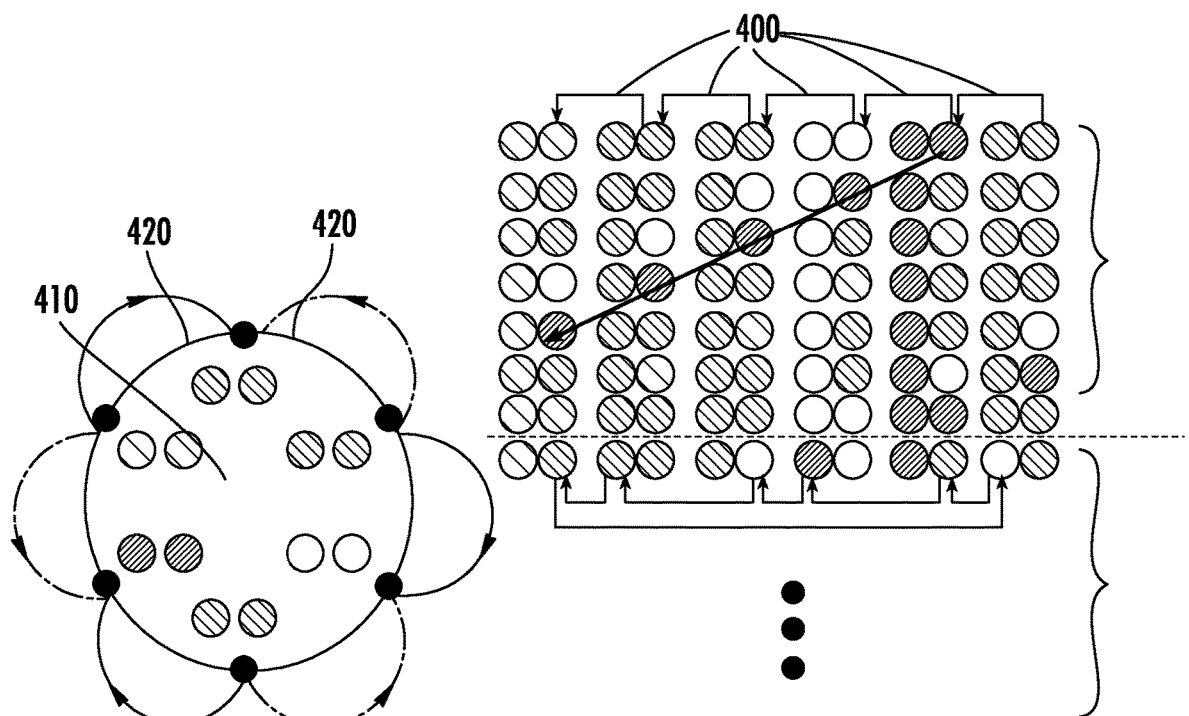
FIG. 4 shows a cross section through the braid.

The braiding process resembles a modified maypole dance (see FIGS. 6-8 for exemplary braiding schemes). In one embodiment, braided probes with 24 wires comprise six bundles of four wires each; at least 12 bundles of 2 wires each control the position of each wire pair in the braid which will may be used for constructing the multi-site probes. Simple algorithms allow for construction of a braid with wires arranged in different combinations through the braid, as shown in FIG. 4 by the simple procession 400. The wires are arranged on the shuttle plate 410 in groups of two 420. The braid structure in FIG. 4 allows the different combination sites to all be accessed along a single line on one side of a braid, reducing the degrees of freedom needed in piece manipulation on a laser manufacturing apparatus and simplifying manufacture of combinatoric braids.

Braided electrode design provides a solution to the need for easy wire recombination, in tissue flexibility and deep placement. Braids support site combination during the braiding process. Braided probes can also be either flexible, or stiffened for insertion by means of a central form or coating, or by using braid jamming behaviors; thus, braided probes are suited for placement anywhere that would be suitable for a multielectrode probe, or needle. Precise insertion is similar to the insertion of a needle or single electrode, but what is left in the tissue consists of a braid of ultrafine, highly compliant wires. The braid topology and mechanical weave constraints will (regardless of stiffness) preserve local spatial relations among combination sites in a tissue.

Where the multi-site probe comprises electrodes, a suitable wire for use in the braid may include 9.6 or 12.7 μm Nichrome wire, which has 4 to 21 times better compliance than a standard, single 50 μm wire. Additionally, 9.7 micron NiChrome wire may be suitable, as it matches or exceeds spatial and compliance properties of those wires which show the best published longevity of recording in a primate (<7 years). It is desirable to keep wire impedance within the 200-250 kOhm range; for some diameters and compositions of wire, electroplating or sonicoplating may achieve this range. The wires may be electroplated with gold and multi-walled carbon nanotubes to achieve down to desirable impedances on the tip of such electrode wires. Electroplating with a gold/MWCNTs slurry may bring individual wire site impedances into the 200-250 Kohm range. For the multi-site wires, the site on a wire to be plated can employ insulating (e.g., oil) gaps at other sites on the wire to isolate along the probe. Alternatively, electroplating may involve sonicoplating using either a platinum solution or a gold solution with MWCNTs.

Laser insulation ablation along a wire is possible and such laser use will allow better control of the precise impedances of the individual sites. An Excimer laser (KrF (248 nm)) is capable of cutting the braids and precisely removing insulation.

Where the multi-site probe comprises optrodes, optical fibers may comprise polymers polyetherimide (PEI), polyphenylsulfone (PPSU), polycarbonate (PC), cyclic olefin copolymer (COC), polymer composites (carbon-loaded conductive PC, CPC, and polyethylene, CPE), and a low melting temperature metal (tin, Sn). A combination of polymers with similar Tg points, different refractive indexes (for the core and the cladding), and high transmission in the visible spectrum may fabricate polymer multi-mode waveguides (WG). PC (Tg=140-145° C.) and COC (Tg=150° C.) may be suitable materials for the waveguide optical core and cladding, respectively; both PC and COC are highly transparent in the visible range. In order to deliver light power densities sufficient for ChR2-facilitated neural excitation, polymer wave guides may use a power input of <50 mW for a device length of 1-5 cm, which is readily accessible with common diode pumped solid state (DPSS) laser systems. The optical WGs may be connectorized to pig-tailed ferrules for ferrule-to-ferrule coupling to laser sources with zirconia sleeves. The cladding of WG fibers is selectively etched along the length of the fiber to enable optical delivery to specific depths along the implant. Further miniaturization of the braid assemblies for optrodes is possible using state of the art wire drawing and fiber drawing methods.

As illustrated in FIG. 1, between the insertion wire 110 and the braid 120 there may a layer 130 of dissolvable material. Upon insertion, this layer 130 of dissolvable material may immediately start to absorb water and dissolve. This may induce not only a lubricated interface between the insertion wire 110 and the braid 120, but also a layer of empty space, thereby facilitating easy, damage free removal of the insertion wire. The small amount of biocompatible dissolvable material will then dissolve away fully. This dissolvable coating 130 may comprise such substances as CMC, trehalose, and glucose. The applicator may apply the coating to the insertion wire 110 through such methods as dip-coating and spray coating. The dip-coating method dips the insertion wire into the dissolvable polymer hydrogel. After the evaporation of the DI water (the solvent used for the aforementioned dissolvable materials), the coating solidifies. This step can also comprise lyophilization or freeze drying of the coating, which induces porosity thereby further accelerating the dissolution of the polymer. The second method is spray coating using a rotary setup. In one embodiment, the insertion wire rotates at 100-500 rpm. A pressurized spray gun applies a low concentration (5-8%) of the dissolvable polymer to the rotating insertion wire. This gun atomizes the polymer-water mixture, with micron-to-sub-micron droplet sizes. The rotation of the wire and the small size of the individual droplets allow uniform application of the dissolvable material onto the wire. After application for a few minutes, the spray stops, and a fan blows heated air onto the wire to remove excess water and to solidify the coating. These steps repeat multiple times until the coating reaches the required thickness. In either method, a user may modify the surface of the insertion wire (e.g., by oxygen plasma cleaning) to enable better adhesion of the polymer onto the wire.

As shown in FIG. 1, the end of the probe 100 is coated with an insulating layer 140 that prevents possible electrical shorting and facilitates a lower-force insertion of the probes that minimizes damage to the tissue. This insulating layer 140 covers the exposed portion of the braided mesh 120, and comprises an electrically insulating, biocompatible and bio-inert polymer. Examples of insulating polymers suitable for this insulating layer 140 include Polydimethylsiloxane (PDMS), Polymethyl methacrylate (PMMA) and Fluorotherm (FEP). Processes may produce this layer by such methods as dipcoating the probe tip 150 using a thermal aging or casting process, or micro-molding the tip 150. For dipcoating, the technician attaches the probes to a precision motion stage, and places the liquid form of the bio-inert polymer on a small container. The probe tip is then dipped into the liquid polymer in a controlled fashion. Subsequently, the tips are removed and allowed to cross-link or cool down to be solidified. For micromolding, a set of molds may be prepared with wells, and the wells may be filled with the liquid polymer. Aligning the tips and placing them in the wells follows. After solidification, the technician separates the probes with the insulated tip coatings from the mold.

On top of this layer 140 is disposed a sharp tip 150 designed to pierce neural tissue 210, which is capable of detaching from the insertion wire 110 upon insertion and eventually either removing from the body or even dissolving within the body. Current insertion methods use a blunt braid with a sharp core which takes significant practice to use. Earlier designs used a 'chaperone tip' to penetrate pia and tissue, to support and protect the braid. This leaves a stiff core behind, obviating many benefits of braids for chronic use. User feedback suggests a permanent or slowly dissolving tip is preferable to the sharp core design, as the sharp core design is hard to use without practice.

This tip can be produced as follows; prepare a master mold with sharp tipped projections using a mechanical micromilling process. Then create PDMS production molds with wells (with the negative shape of the sharp tips) from the master mold. Then uses desired amounts of dissolvable polymer (as a hydrogel) to fill the wells of the PDMS production molds. Subsequently, a centrifuging process reduces the solvent (water) concentration to 60 wt. %-40 wt. % level. Next, using special attachment and alignment features, place the insulated tips of the probes inside the hydrogel. The PDMS mold with the probes is then placed into a vacuum oven to fully evaporate solvent. After the evaporation, probes with sharp insertion tips are separated from the PDMS molds.

Figure 5:
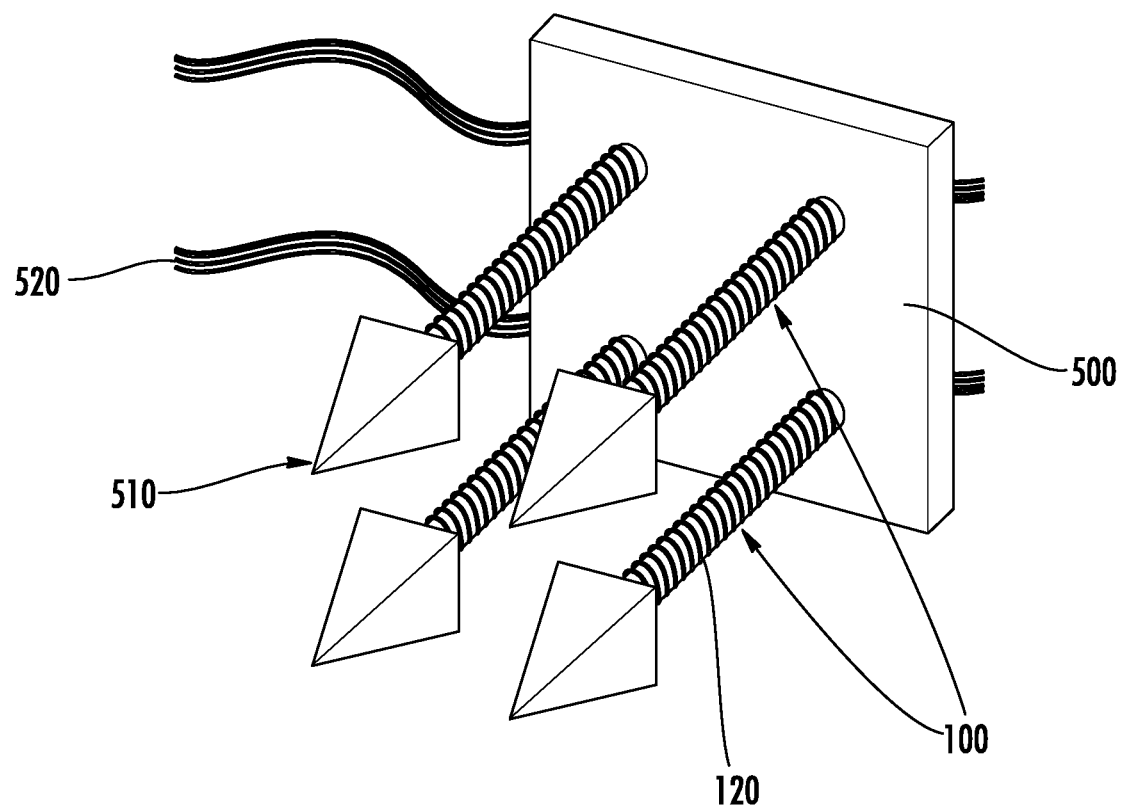
FIG. 5 shows elements multiple probes on a backing layer.

As shown in FIG. 5, one or more individual probes 100 may be placed into a rigid backing layer 500 through molding and precision assembly techniques while ensuring that the probes 100 are standing out of plane and will be perpendicular to the surface of the backing layer 500. This completes the multi-site probe 510. The backing layer 500 may be made of resin. For each probe 100, the braid 120 connects through the backing layer 500 to a tether cable 520, which transmits electrical or optical signals to and from the probe 100. The tether cable 520 may be attached to an off-the-shelf headstage connector that uses gold pinning to secure the wires on the connector. The base of the connector board may be small, as the smaller the base the more ideal it is for precision applications, although larger bases are suitable for proof-of-concept applications.

These multi-site probes represent a distinct improvement over the current methods; namely, they offer lower long term inflammatory responses and higher probe compliance and tolerance of micromotion, lower local long-term diffusion barrier in the tissue due to the open lattice of the braid and open lumen of the braid tube, coupled with means for precise deployment in deep brain, in cortex, or in spinal cord CNS targets.

Figures 6A, 6B, 6C:
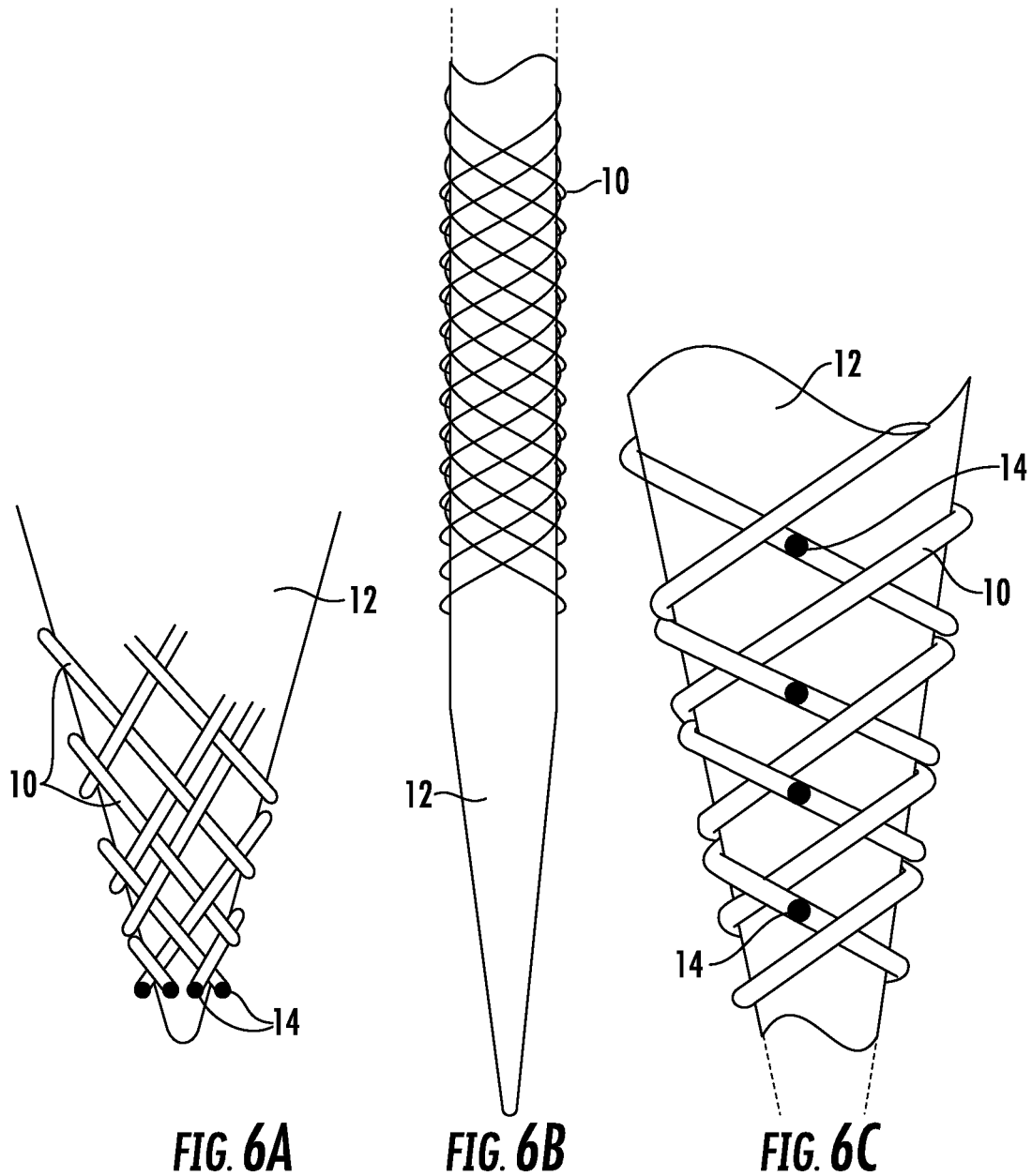
FIG. 6 depicts partial schematic views 6A, 6B, and 6C, of exemplary embodiments of a microbraided sensing probe.

FIG. 6 depicts partial schematic views of an exemplary embodiment of a microbraided probe. Such a probe as shown in FIG. 6 and also 7 and 8, as mentioned herein, may be used both for delivery of light through optrodes, as well as sensing. Thus combinatoric advantage may be had in both sensing and delivery. FIG. 6 depicts relatively simple braided probes (e.g., Maypole braid) in accordance with example configurations of the probe comprising multiple, spatially separate, sensing sites. For example, fibers 10 are braided together over a braiding form 12. FIG. 6A shows a conical structure for the tip of the probe. It also shows sites on the conductive fibers that are exposed to the environment and useful for sensing/delivering electrical potential, for achieving differential electrical stimulation, or both. In an example embodiment, these are regularly arrayed in a geometric pattern defined by the braid. In this embodiment, the braiding form may also be active. For example, the form may be a fiberoptic device, a cannula, a micropipette or other element, which is itself useful intracorporeally. FIG. 6A shows one sensing/actuation site per conductor for the sake of simplicity. It is to be understood however, that multiple sites per conductor are applicable. While in FIG. 6, each filament or fiber 10 is depicted a being a single conductor, insulated except for at the activation/sensing site, each filament or fiber can also comprise pluralities of individual conductors or other fibers, fibrils, or filaments. In such cases, increased density of conductors and actuation/sensing sites can be achieved.

FIG. 6B shows how a tubular braided sensing probe can be made by braiding fibers 10 over braiding form 12. Change in the geometry of the probe can be achieved through appropriate shaping of the form, here into a pencil-like shape. It is also useful to form the braided probe into a simple tubular configuration for many embodiments, whereupon use of a conical section is not made. FIG. 6C depicts a conical braiding arrangement of the probe tip with sensing/stimulation sites 14 arrayed generally longitudinally along the braid.

Figures 7A, 7B, 7C:
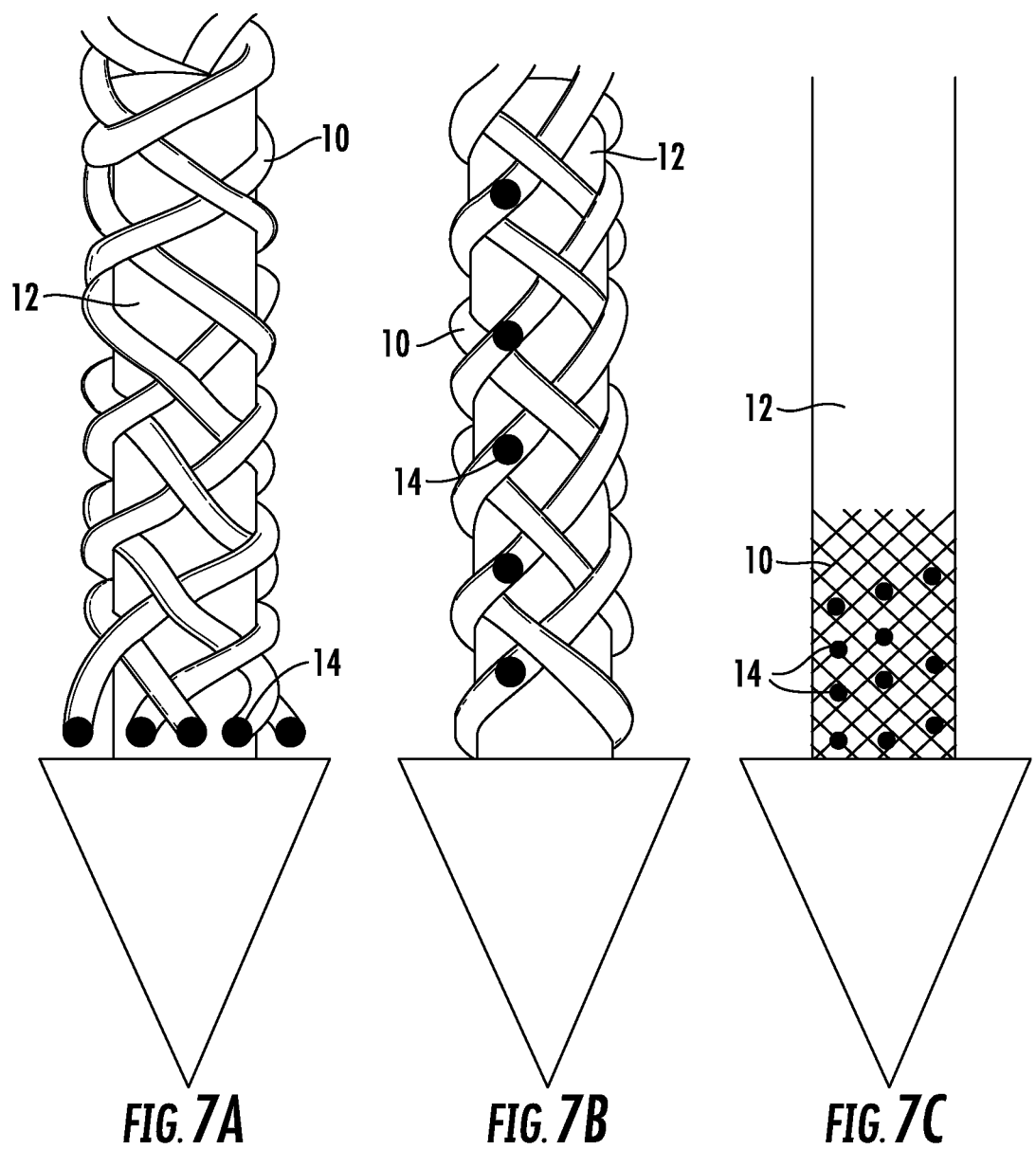
FIG. 7 depicts example sensing sites on a braided sensing probe for example embodiments 7A, 7B, and 7C.

FIG. 7 depicts sites on a braided sensing probe. FIGS. 7A, 7B and 7C show three embodiments, each generally tubular in braid structure. FIG. 7 depicts different arrangements and geometries of sensing/stimulation sites on the braids. A single conductor can communicate with pluralities of sites or vice versa. FIG. 7 is intended to imply that the braided probes can be removed from the braiding form after formation and used independently and in different configurations. Such release can be performed after insertion intracorporeally or otherwise.

Figures 8A, 8B, 8C:
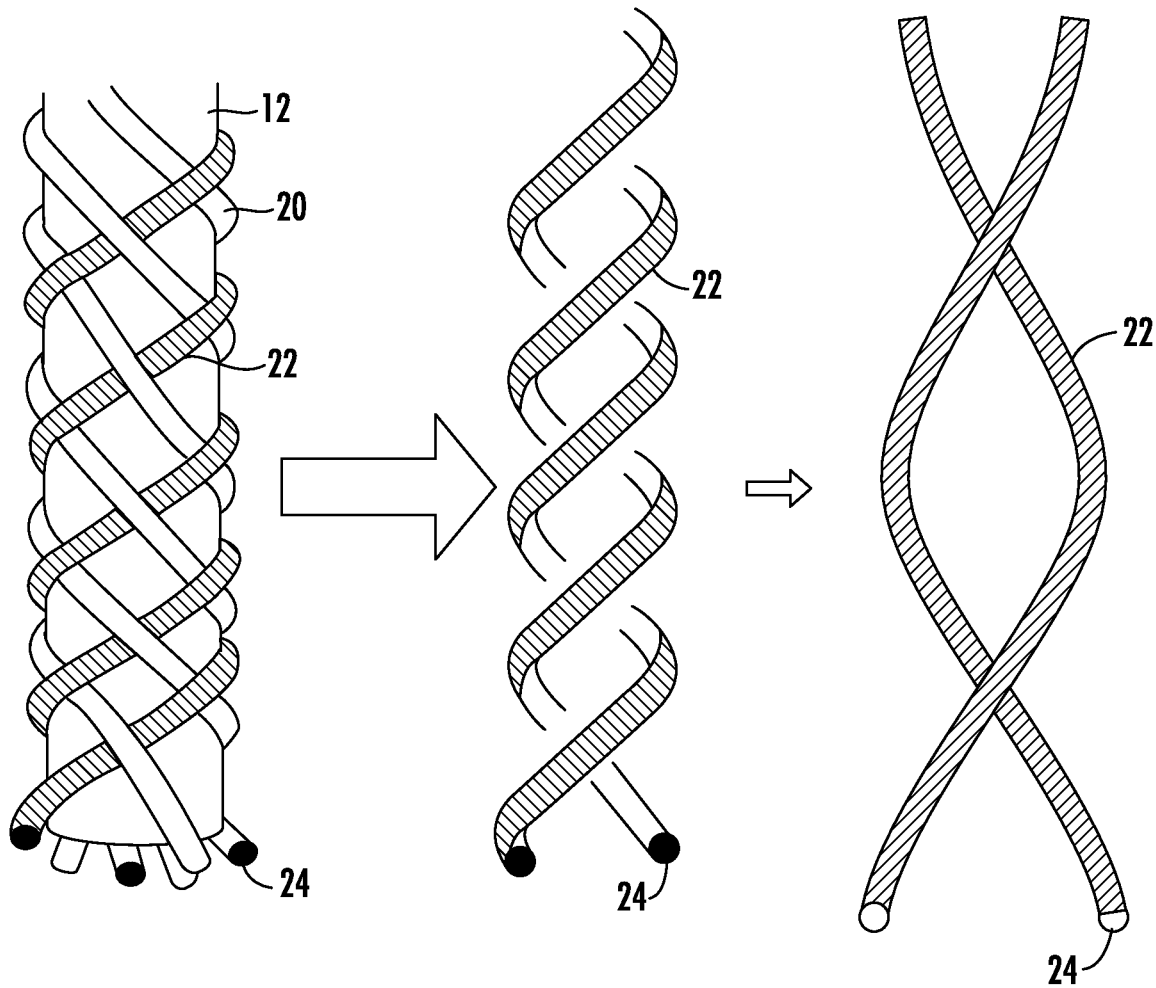
FIG. 8, including 8A-8C, depicts certain biodegrading elements which dissolve or degrade in vivo leaving areas of exposed conductor behind on non-biodegradable elements.

FIG. 8 depicts example biodegrading elements which dissolve or degrade in vivo leaving areas of exposed conductor behind on non-biodegradable elements. FIG. 8A is of a tubular braided probe comprising conducting, biologically stable filaments 22 and biologically soluble or degradable filaments 20 braided together over a form 12. As shown, the two types of fibers are braided clockwise and anticlockwise. In this case, the braided probe, formed of both degradable or soluble fibers and non degradable or insoluble fibers, can be removed from the braiding form after braiding. After exposure to biological conditions or to solvent, stable filaments 22, most or all of which include conducting elements, are released and form a new geometry, here a helical pattern. FIGS. 6B and 6C depict this along with the sensing/stimulation sites 24. The geometry can further change, as shown, by relaxing, or otherwise. In this way, relative small, loosely organized conductors can be delivered to a biological situs in a relatively rigid, structured form and released to assume a relative loose, form. This arrangement permits delivery of very small sensing probe units and ones having minimal impact upon the organism into which the sensing probes have been implanted.

Combinatoric Method

Coupling the proposed multi-site probes with a method of positioning them on the body facilitates subsequent separation of units recorded at different sites on the wire and thereby enables useful signal processing strategies. In recording, it is possible to monitor more than one site on each wire or channel (i.e., wires or optic fibers can now be multi-site) in such probes, without loss of spatial precision, if the site elements used for recording on the wires conform to a precise pattern of combinations in the tissue. For such multi-site probes, the use of precise patterning of the recording sites in combinations will enforce correlations of discrete action potential signals recorded on subsets of wires from a given spatial location. The presence of these correlations may allow for separation of the signals through modern signal processing methods to precisely identify the location of the signal's origin.

The proposed method comprises the use of combinatorics in placing the multi-site probes. The combinatoric design uses the rapid expansion of the numbers of uniquely identifiable spatial locations and wire combinations possible with an increasing number of wires and numbers of sites on the wires. The rapid explosion of possible combinations allows a large expansion of the number of spatial locations in the CNS that are concurrently sampled using multi-site wires, together with algorithms to separate the signals from the different spatial locations recorded on the probe.

Combinatorics the branch of mathematics studying the enumeration, combination, and permutation of sets of elements and the mathematical relations that characterize their properties. This math underpins the proposed method strategy. The strategy exploits combinatorics to organize large numbers of multisite wires. Combinations of items selected from larger sets can rapidly become huge. To grasp the power of this approach, consider the following: There are only three ways to choose 2 items from 3. However, there are 15 ways to choose 2 items from 6. This means that organizing 6 multi-site probes into combinations of two sites results in 15 sites. Each multi-site probe will necessarily participate in 5 combinations, and so should have no more than 5 sites. These combination site locations are usable for differential recordings relative to a reference. At each combination location the two probe sites at that location will generate recordings that will possess specific correlations of their action potentials, but these will mix on the wire with the signals picked up from other sites.

Using these specific correlations of discrete action potential events and the combination map to separate these mixed signals may locate the recorded unit's spatial origin on the probe. Extending this picture to more multi-site probes and more combinations, the numbers rapidly increase. There are 66 ways to choose 2 items from 12, but 495 ways to choose 4 items (i.e., tetrode combinations at locations) from 12, and 10,626 ways to choose 4 items from 24. Thus, with 24 wires, if neural firing was sufficiently sparse, more than ten thousand tetrode spatial locations could be defined from combinations of the multi-site probes. More conservative designs in defining tetrodes when considering spike (action potential) coincidences on multiple tetrodes, digitization resolution and noise, or other issues that might degrade the ability to achieve high resolution signal separation. Exploiting only a twentieth of the tetrode combinations possible in the "24 Choose 2" case using multisite probes, however, could nonetheless have >500 tetrodes using 24 probes, or almost two orders of magnitude more tetrodes available than the 6 tetrodes that could build conventionally using 24 probes.

The significance of such potential gains may be within a fixed form factor implant that may increase single unit yield per wire and the numbers of sites recorded electrically or stimulated optically by a factor of from four to eight, or perhaps more. Further, a designer may customize the numbers of probes co-located at the combination sites: sites on a given probe could be hexode, or octode rather than tetrode if desired, with these potentially enabling more sophisticated signal processing at each combination site. Additionally, the application of combinatorics shows improvements in spike yield per wire over conventional methods as well as recovered source location along the probe. These locations could (in a long braided probe) each be in different brain regions or different parts of nuclei, an advantage for studies focusing on interactions within or among nuclei.

One embodiment employs the following principles for multisite wire combinations and algorithms for subsequent recording analysis. It is possible to record multiple classifiable single unit action potentials from multiple 5-10 µm exposed recording sites along a 10 µm tungsten microelectrode. Signals from separate 200 Kohm recording sites along one electrode wire will roughly add. Wire impedance is negligible compared with recording site impedance. The multisite wire therefore acts as a summing or mixing junction for the neural sources originating at each recording site along its length. Defining multisite wire combinations may be enumerated based on the numbers of wire (n) and the numbers of wires combined at a combination site (k) as the operation n Choose k (abbrev. nCk). nCk is enumerated as:

$$_nC_k = \frac{n!}{(n-k)!\,k!} \quad \text{(Equation 1)}$$

Consider 3 wires taken in pairs. 3C2=3. Each wire can be made multi-site, with two sites, each paired with one other wire. The neurons recorded on each of the two sites on a single wire form signals on the wire that are mixed together and must be unmixed. This is a classical well-posed blind separation of sources problem. Blind separation of sources is the cocktail party problem of picking conversations out in a room full of noise where Independent Components Analysis (ICA) helps achieve sound separation. One embodiment uses an Infomax variant implemented in MATLAB. Consider 6 wires with multisites arranged into pairs. 6 Choose 2 is the number of sites. Unfortunately, for the simple ICA method 6C2 is 15. But 6 wires can only separate 6 sources. However, the combination strategy for recording may also indicate one solution.

Virtual wires, 30 in all, may represent the signals of each wire at each specific site. When no spike collision occurs, just as in real world recording systems, a system can excerpt the spike from the time series. When spikes occur on two wires simultaneously and nowhere else on the interval, the spikes can be readily assigned to the virtual wires at that site using knowledge of recording probe's structure, i.e., in situations where the signal is not blinded and information is available. Placement of all such pure spikes on the appropriate virtual wires may assign them to locations. Effectively these signals are unmixed based on their clean coincidence. For brain regions with low firing rates this may be sufficient to lose relatively few spikes to the 'nowhere else' discussion noted above, and relatively little spike information may be lost by omitting the potentially ambiguous collisions (in our simulations at 10 Hz 4.6% of spikes were lost to such collisions, at 20 Hz 9.2% and at 30 Hz 12.1%). However, this rate of loss may be unacceptable. If spike coincidence is an important encoding mechanism in a brain area, this heuristic of dropping all collisions on the probe from analysis would omit the events of most interest.

When spikes at different site locations collide in time, the sensors record spikes on more than two wires at a time and are mixed. In some cases, the wires do not have common sites, and this presents no difficulty in the analysis. However, often signals can occur on wires shared at 2 sites thereby causing potential ambiguity. Unsurprisingly, this is more frequent at higher rates and higher firing rate periods are often the more interesting times to analyze activity. Collision management is a key issue in such probes.

Various heuristic and principled strategies to manage collisions on the wires, and to assign signal to virtual wires could be possible. One heuristic is to place all the collision data on the appropriate virtual wires, based on the possible sites involved, and thus trying to capture the degree of ambiguity. Managing total signal power may be done by dividing the signals by the numbers of wires they are duplicated on. A spike activity coincidence on three wires could only come from collisions originating at three sites, so it is placed only on the virtual wires representing recording at those sites, and so on for four wires with shared sites.

At this point, when whatever assignment heuristic or signal processing method is completed, the process has distributed original spike information, from 6 wires in the 6C2 simulation example, across 30 virtual wires and has segregated it in patterns that reflect the probability of possible origin given the known wire/site structure. The method thereby organizes the problem for blind source separation into a matrix that is 30×N where N is the recording length. Tuning the creation of signals on the 30 virtual wires may reflect several known structural relations in the data. An ideal heuristic now gives blind separation of source methods 'freedom to operate' to extract 30 sources, some representing the separate wire signals at each site. Accordingly, applying ICA to the 30 virtual wires may seek to cleanly separate the original combination site sources. Applicants have used this method in proof of concept simulations of a 6C2 probe recording units at each site, with simple signal heuristics. Applicants ran the simulation at multiple spike rate intensities using Poisson spike generation. To simulate real world ambiguities, in simulations applicants dropped higher order collision spikes from the virtual wire recordings. Recovery of spikes was very good at low rates (<15 Hz), even after loss of higher order signals and their statistics from the ICA setup runs. In effect, the simulation showed wires in the 6C2 multi-site wire arrangement could record almost 5 times more activity than single site wires, and assign that activity to locations with only a little loss of signal fidelity in some cases. More sophisticated signal processing should be able to significantly improve on this, for higher rate activity and collisions, using more of the structural and waveform information. These initial simulations show that the combinatoric design strategy and one proposed signal decomposition methods can support increased yield per wire on the order of our hypothesis (>4× current yield).

One may also apply the proposed combination of multi-site wire and combinatorics to optical stimulation, by using fiber optic optrodes with multiple spatially separated light release sites to combine light to suprathreshold intensity only at an addressed location on a probe. In addition, any multi-electrode design platform that supports precise 3D rearrangements of fiber and wire geometry in combinatoric arrangements may support the proposed combination in the future.

While the invention has been described with reference to the embodiments above, a person of ordinary skill in the art would understand that various changes or modifications may be made thereto without departing from the scope of the claims.

The invention claimed is:

1. A probe, comprising:
   a plurality of electrical conductors, each electrical conductor of the plurality of electrical conductors comprising a plurality of delivery sites; and
   a plurality of combined delivery sites configured to deliver light, each combined delivery site of the plurality of combined delivery sites being formed by proximate portions of multiple electrical conductors of the plurality of electrical conductors, each combined delivery site of the plurality of combined delivery sites being spatially separate,
   wherein no two combined delivery sites are formed by a same combination of electrical conductors,
   wherein the electrical conductor is formed from a braid of electrically conductive wires,
   wherein the braid comprises fiber optic optrodes, and one or more fiber optic optrodes of the fiber optic optrodes comprise multiple spatially separated light emitting sites to combine the light for attainment of a suprathreshold intensity and emit the combined light that acts as a potential stimulator, and
   wherein the braid allows the different combined delivery sites to be accessed along a single line of the braid that emits light.

2. The probe of claim 1, wherein the plurality of electrical conductors is formed as a braid.

3. The probe of claim 2, wherein the braid of the plurality of electrical conductors is formed around a core.

4. The probe of claim 3, wherein the core is made of tungsten.

5. The probe of claim 1, wherein the electrically conductive wires are made of an alloy principally comprising nickel and chromium.

6. The probe of claim 1, wherein the electrically conductive wires are less than 50 microns in diameter.

7. The probe of claim 1, wherein the braid comprises fiber-optic waveguides.

8. The probe of claim 1, wherein stimulation occurs at a threshold, and the emitted light from any one fiber optic optrode is emitted below the threshold.

9. The probe of claim 1, wherein stimulation occurs at a threshold, and the emitted light from a combination of the fiber optic optrodes is emitted above the threshold.

10. The probe of claim 9, wherein the stimulation occurs based on a combinatoric delivery of light through the fiber optic optrodes.

11. The probe of claim 1, comprising an electrically insulating layer disposed between a pointed tip and the braid.

12. The probe of claim 11, where the electrically insulating layer is made of one or more materials selected from a group consisting of: polydimethylsiloxane (PDMS), polymethyl methacrylate (PMMA), and fluorotherm (FEP).

13. The probe of claim 11, wherein the electrically insulating layer is made using one or more means selected from a group consisting of: dip-coating and micro-molding.

14. The probe of claim 1, wherein the braid is formed as a maypole of the electrically conductive wires.

15. The probe of claim 1, wherein each delivery site of the plurality of delivery sites is also a sensing site, capable of recording data.

16. The probe of claim 1, wherein one or more probes are disposed perpendicularly on a backing layer, and wherein each probe of the one or more probes comprises a braided electrical conductor formed as a braided sleeve over a flexible or rigid delivery-vehicle.

17. The probe of claim 1, wherein at least some electrical conductors of the plurality of electrical conductors are separated from each other at delivery sites.

18. The probe of claim 1, wherein a position along the probe on a patient's body is selected using combinatorics.

19. The probe of claim 3, further comprising a layer of dissolvable material between the braid and the core, wherein when the dissolvable material gets dissolved, a lubricated interface and a layer of empty space is induced between the braid and the core.

* * * * *